US00PP35430P2

(12) United States Plant Patent
Lim

(10) Patent No.: US PP35,430 P2
(45) Date of Patent: Oct. 24, 2023

(54) CLIMBER ROSE PLANT NAMED 'LIMPROFESSORLEENEAN'

(50) Latin Name: *Rosa hybrida*
Varietal Denomination: LIMprofessorleenean

(71) Applicant: Altman Specialty Plants Inc, Vista, CA (US)

(72) Inventor: Peter Lim, Escondido, CA (US)

(73) Assignee: Altman Specialty Plants Inc, Vista, CA (US)

( * ) Notice: Subject to any disclaimer, the term of this patent is extended or adjusted under 35 U.S.C. 154(b) by 0 days.

(21) Appl. No.: 18/091,789

(22) Filed: Dec. 30, 2022

(51) Int. Cl.
*A01H 5/02* (2018.01)
*A01H 6/74* (2018.01)

(52) U.S. Cl.
USPC ..... Plt./114
CPC ..... *A01H 6/749* (2018.05)

(58) Field of Classification Search
USPC ..... Plt./148, 114
CPC ..... A01H 5/0222
See application file for complete search history.

*Primary Examiner* — Kent L Bell
(74) *Attorney, Agent, or Firm* — Cassandra Bright

(57) ABSTRACT

A new and distinct cultivar of *Rosa* plant named 'LIMprofessorleenean' is disclosed, characterized by late blooming, light pink double flowers with a tea rose fragrance. Plants are vigorous, low climbing, and can be grown on their own roots. The new variety is a *Rosa*, normally produced as an outdoor garden or container plant.

1 Drawing Sheet

Latin name of the genus and species: *Rosa hybrida.*

Variety denomination: 'LIMprofessorleenean'. cl BACKGROUND OF THE INVENTION

The new *Rosa* cultivar is a product of a planned breeding program conducted by the inventor, Peter Ping Lim. The objective of the breeding program was to produce vigorous new garden rose varieties with continuous blooming for ornamental commercial applications. The cross resulting in this new variety was made during June of 2011 in McMinnville, Oreg.

The seed parent is the unpatented variety *Rosa* 'AUSblush'. The pollen parent is the unpatented variety *Rosa* 'High Voltage'. The new variety was selected in June of 2012 by the inventor in a group of seedlings resulting from the 2011 crossing, in a nursery in McMinnville, Oreg.

Asexual reproduction of the new cultivar has been performed by vegetative cuttings. This was first performed at a research greenhouse in Vista, Calif. in July of 2013 and has shown that the unique features of this cultivar are stable and reproduced true to type in more than 5 successive generations.

SUMMARY OF THE INVENTION

The cultivar 'LIMprofessorleenean' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LIMprofessorleenean'. These characteristics in combination distinguish 'LIMprofessorleenean' as a new and distinct *Rosa* cultivar:

1. Double light pink flowers.
2. Typical tea-rose flower shape with the central petals standing higher than the outer petals, forming an inverted cup-shape.
3. Light glossy foliage resistant to black spot and powdery mildew disease.
4. Late blooming.
5. Low climbing plant.
6. Continues flowering after second year.
7. Plants can be grown on their own roots; grafting is not required.

PARENT COMPARISONS

Plants of the new cultivar 'LIMprofessorleenean' are similar to plants of the seed parent, in most horticultural characteristics, however, plants of the new cultivar 'LIMprofessorleenean' differ in the following:

1. Flower color of the new variety is a deeper pink than flowers of the seed parent.
2. Flowers of the new variety have more petals than flowers of the seed parent.
3. Plants of the new variety are about 6 to 7 feet in height at maturity, while plants of the seed parent are about 4 to 5 feet in height at maturity.

Plants of the new cultivar 'LIMprofessorleenean' are similar to plants of the pollen parent in most horticultural characteristics, however, plants of the new cultivar 'LIMprofessorleenean' differ in the following:

1. Flower color of the new variety is light pink, while flower color of the pollen parent is yellow.

COMMERCIAL COMPARISONS

Plants of the new cultivar 'LIMprofessorleenean' can be compared to the commercial variety *Rosa* 'AUStiger', U.S.

Plant Pat. No. 17,150. These varieties are similar in most horticultural characteristics, however 'LIMprofessorleenean' differs in the following:

1. Flowers of the new variety have more petals than flowers of this comparator.
2. Flowers of the new variety have a moderate tea rose fragrance, while flowers of this comparator have a myrrh fragrance.
3. Plants of the new variety are about 6 to 7 feet in height at maturity, while plants of this comparator are about 4 feet in height at maturity.

Plants of the new cultivar 'LIMprofessorleenean' can also be compared to the commercial variety *Rosa* 'New Dawn', U.S. Plant Pat. No. 1. These varieties are similar in most horticultural characteristics, however 'LIMprofessorleenean' differs in the following:

1. Flowers of the new variety have more petals than flowers of this comparator.
2. Flowers of the new variety are a deeper pink than flowers of this comparator.
3. Plants of the new variety are about 6 to 7 feet in height at maturity, while plants of this comparator are about 5 to 6 feet in height at maturity.

BRIEF DESCRIPTION OF THE PHOTOGRAPH

The accompanying photograph illustrates in full color a close up of an individual flower from a plant of about 18 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'LIMprofessorleenean' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'LIMprofessorleenean'.

Market classification: Climber rose.

PROPAGATION

Time to initiate roots: About 15 days at approximately 20° C.

Time to produce a rooted cutting: About 35 days at approximately 20° C.

PLANT

Age of plant described: Approximately 1.5 years.

Growth habit: Low climber, about 6 to 7 feet in height at maturity.

Container size: 2 gallon.

Height: 60 cm.

Plant spread: 80 cm.

Rootstock: Own root.

Growth rate: Vigorous.

Branching characteristics: Sympodial branching.

Length of primary lateral branches: Average range 15 to 32 cm.

Diameter of primary lateral branches: Approximately 10 mm.

Quantity of branches: 4 to 6 main branches, moderate lateral branches, 10 to 20 lateral branches per main branch.

Branches—young wood:

*Diameter.*—Approximately 6 mm.

*Texture.*—Glabrous, very few thorns.

*Color.*—Near RHS Green 137B.

Branches—old wood:

*Diameter.*—Approximately 10 to 14 mm.

*Color.*—Near Green 137B, striated Greyed-Orange 175A.

*Texture.*—Glabrous with some striations on oldest wood.

*Thorns.*—Approximately density/quantity of thorns: Sparse. Less than 1 per 1 linear cm of stem on average. Young growth: Approximately 4 mm in diameter at base and 4 to 5 mm long. Colored near RHS Yellow-Green 144C. Mature growth: About 7 mm at base, 6 mm long. Colored near RHS Grey-Orange N170B. Moderately hooked.

FOLIAGE

Leaf:

*Arrangement.*—Alternate and compound.

*Quantity.*—Average 10 to 16 per main branch.

*Internode.*—Average 3.5 cm.

*Average length.*—Approximately 10 to 11 cm.

*Average width.*—Approximately 7 to 8 cm.

Rachis:

*Average length.*—Approximately 3 cm.

*Average diameter.*—Approximately 2 mm.

*Color.*—Upper surface: Near RHS Yellow-Green 144B. Lower surface: Near RHS Green 143C.

*Texture.*—Upper Surface: Glabrous. Lower Surface: Glabrous with a single small sharp thorn at lowest leaflet pair. Thorn about 2 to 3 mm long, colored near RHS Green 143C.

Leaflet:

*Quantity.*—5.

*Average length.*—Approximately 3.5 to 4.5 cm.

*Average width.*—Approximately 2.5 cm.

*Shape of blade.*—Ovate.

*Apex.*—Acute.

*Base.*—Broadly rounded.

*Margin.*—Serrate.

*Appearance of top surface.*—Glossy.

*Appearance of bottom surface.*—Matte.

*Texture of top surface.*—Glabrous.

*Texture of bottom surface.*—Glabrous.

*Color.*—Young foliage upper side: Near RHS Yellow-Green N144A. Young foliage under side: Near RHS Yellow-Green 144C. Mature foliage upper side: Near RHS Green 143C. Mature foliage under side: Near RHS Yellow-Green 144C.

*Venation.*—Type: Reticulate. Venation color upper side: Near RHS Yellow-Green N144C. Venation color under side: Near RHS Yellow-Green N144D.

Petiole:

*Average length: Approximately* 2.8 cm.

*Average diameter. Approximately* 2 mm.

*Color*.—Upper surface: Near RHS Yellow-Green 144B. Lower surface: Near RHS Yellow-Green 143C.

*Petiole wing*.—Typically 12 mm long and 6 mm wide. Apex apiculate. Upper surface colored near RHS Yellow-Green 144C, lower surface colored near Yellow-Green 144B.

*Texture*.—Glabrous.

FLOWER

Natural flowering season: Spring until Autumn.

Inflorescence type and habit: Singly occurring fully double rotate flowers. Raised center of flower.

Rate of flower opening: Approximately 7 days from bud to fully opened flower.

Flower longevity on plant: About 1 to 1.5 weeks.

Quantity of flowers: 20 to 30 fully opened flowers and buds.

Flower shape:

*From above*.—Round to very slightly irregular round.

*Profile of upper part of flower*.—Conical.

*Profile of lower part of flower*.—Nearly flat.

Flower size:

*Diameter*.—Approximately 6 cm.

*Height*.—Approximately 3 cm.

Peduncle:

*Length*.—Average 5 cm.

*Diameter*.—3 mm.

*Color*.—Near RHS Yellow-Green 144B.

*Texture*.—Glabrous.

Petals:

*Petal arrangement*.—Multiple rotate, overlapping whorls.

*Petal quantity*.—Average 65.

*Length*.—Average 2 cm.

*Width*.—Average 1.5 cm.

*Shape*.—Obovate.

*Margin*.—Entire, slightly ruffled.

*Apex*.—Rounded, irregularly notched.

*Base*.—Very broad attenuate.

*Texture*.—Glabrous all surfaces.

*Color*.—When opening: Upper surface: Near RHS Red 49A. Very small basal blotch near White N155C. Lower surface: Near RHS Red 49A. Very small basal blotch near White N155C. Fully opened. Upper surface: Near RHS Red 55D. Very small basal blotch near White N155C. Lower surface: Near RHS Red 55D. Very small basal blotch near White NN155C. Aging: Upper surface: Near RHS Red 55C. Very small basal blotch near White N155C. Lower surface: Near RHS Red 55D. Very small basal blotch near White N155C.

Bud:

*Shape*.—Ovate.

*Length*.—Approximately 2.2 cm.

*Diameter*.—Approximately 1.5 cm.

*Color*.—Near RHS Red 49A.

Sepals:

*Quantity*.—5.

*Length*.—2 cm.

*Width*.—7 mm.

*Shape*.—Deltoid.

*Apex*.—Apiculate. Strong sepal extensions.

*Margin*.—Entire.

*Texture*.—Upper Surface: Pubescent. Lower surface: Glabrous.

*Color*.—Interior Surface: Near RHS Green 143C. Exterior Surface: Near RHS Yellow-Green 144C.

Receptacle:

*Length*.—9 mm.

*Width*.—11 mm.

*Shape*.—Hemispherical.

*Color*.—Near RHS Yellow-Green 145C.

Fragrance: Moderate tea rose scent.

REPRODUCTIVE ORGANS

Stamens:

*Quantity*.—About 70. Very densely clustered.

*Filament length*.—Approximately 3 mm to 4 mm.

*Filament color*.—Near RHS Yellow 13D.

Anthers:

*Length*.—2 mm.

*Shape*.—Narrow globular.

*Color*.—Near RHS Greyed-Orange N163A.

*Pollen*.—Color: Near RHS Greyed-Orange N163A. Quantity: Scant or none.

Pistil: Not observed.

OTHER CHARACTERISTICS

Seeds and fruits: Not observed.

Disease/pest resistance: Good overall resistance to normal pests of garden roses. Very good resistance to blackspot (*Diplocarpon rosae*) and powdery mildew (*Podosphaera pannosa*) diseases. In a three-year confidential field trial of garden roses the new variety 'LIMprofessorleenean' remains free of powdery mildew year-round while varieties planted nearby showed symptoms of powdery mildew.

What is claimed is:

1. A new and distinct cultivar of *Rosa* plant named 'LIMprofessorleenean' as herein illustrated and described.

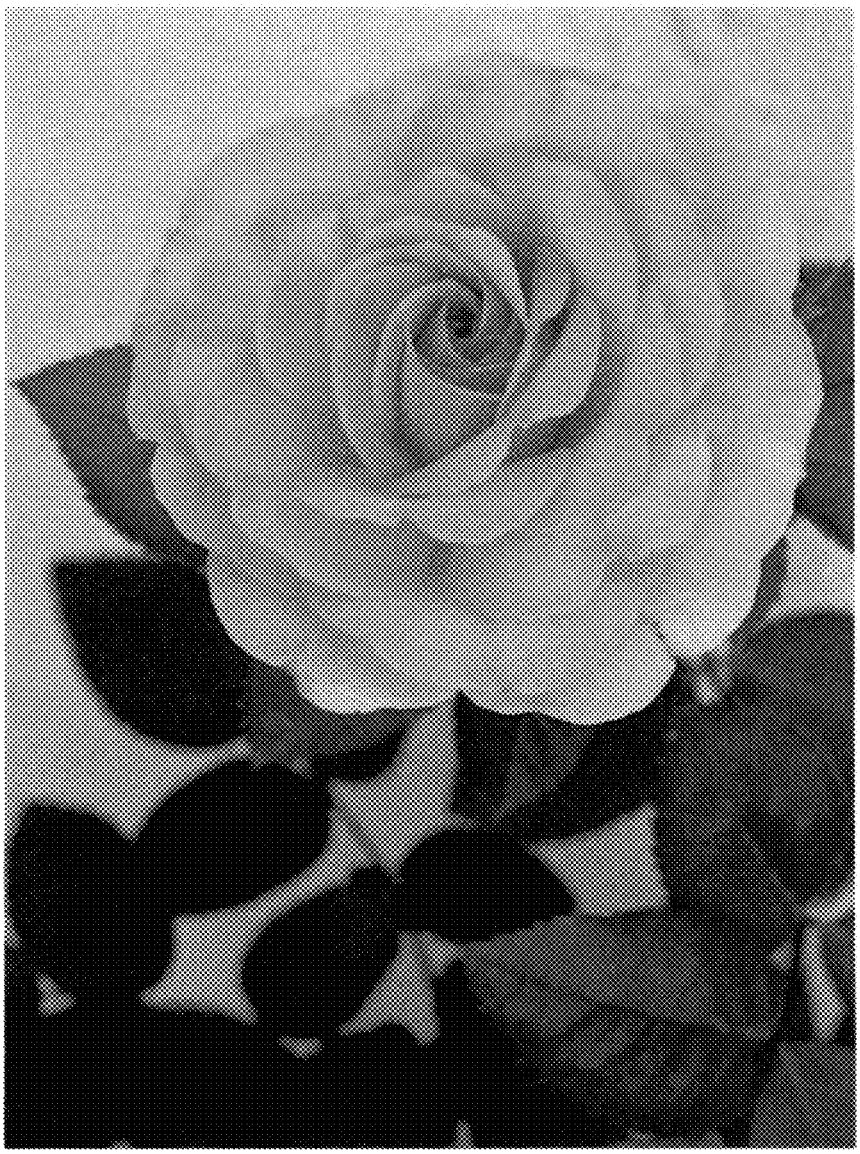

* * * * *